(12) United States Patent
Schmidt et al.

(10) Patent No.: US 12,004,894 B2
(45) Date of Patent: Jun. 11, 2024

(54) MARKER AND SIGNAL DEVICE FOR INDICATING THE PRESENCE OF A LASER

(71) Applicants: Grant Michael Schmidt, Ardmore, PA (US); Richard George Schmidt, Bryn Mawr, PA (US)

(72) Inventors: Grant Michael Schmidt, Ardmore, PA (US); Richard George Schmidt, Bryn Mawr, PA (US)

( * ) Notice: Subject to any disclaimer, the term of this patent is extended or adjusted under 35 U.S.C. 154(b) by 275 days.

(21) Appl. No.: 17/651,939

(22) Filed: Feb. 22, 2022

(65) Prior Publication Data

US 2022/0296199 A1  Sep. 22, 2022

Related U.S. Application Data

(60) Provisional application No. 63/200,586, filed on Mar. 16, 2021.

(51) Int. Cl.
*A61B 6/04* (2006.01)
*A61B 6/00* (2006.01)

(52) U.S. Cl.
CPC ............ *A61B 6/547* (2013.01); *A61B 6/0492* (2013.01); *A61B 6/4441* (2013.01)

(58) Field of Classification Search
None
See application file for complete search history.

(56) References Cited

U.S. PATENT DOCUMENTS

| | | | |
|---|---|---|---|
| 4,194,122 A | 3/1980 | Mitchell et al. | |
| 4,985,019 A | 1/1991 | Michelson | |
| 5,193,106 A | 3/1993 | DeSena | |
| 5,216,700 A | 6/1993 | Cherian | |
| 5,368,030 A | 11/1994 | Zinreich et al. | |
| 5,469,847 A | 11/1995 | Zinreich et al. | |
| 5,702,128 A | 12/1997 | Maxim et al. | |
| 6,333,970 B1 | 12/2001 | LeMaitre et al. | |
| 7,853,311 B1 | 12/2010 | Webb | |
| 8,075,184 B2 | 12/2011 | King et al. | |
| 9,186,225 B1 | 11/2015 | Pettis | |
| 9,375,189 B1 | 6/2016 | Alsahhaf | |
| 9,649,080 B2 | 5/2017 | Kwak et al. | |
| 10,413,377 B2 | 9/2019 | Capote et al. | |
| 2011/0098574 A1* | 4/2011 | Hwang | A61B 5/1127 600/595 |
| 2018/0333208 A1* | 11/2018 | Kotian | A61B 90/13 |
| 2019/0079189 A1* | 3/2019 | Weber | G01S 17/10 |
| 2019/0255654 A1* | 8/2019 | Beckett | B23K 26/0643 |
| 2020/0337670 A1 | 10/2020 | Gorges et al. | |
| 2021/0267692 A1* | 9/2021 | Lennartz | A61B 34/20 |

\* cited by examiner

*Primary Examiner* — Hoon K Song
(74) *Attorney, Agent, or Firm* — Dunlap Bennett & Ludwig, PLLC

(57) ABSTRACT

The present invention relates to the positioning of a laser emitted by a medical device, such as a C-arm X-ray machine. A marker is, in use, positioned on a patient's body, and includes at least one sensor that senses the presence of the laser. A signal emitter is operably coupled to the marker and emits an observable signal, such as a colored light, when the at least one sensor is struck by the laser.

5 Claims, 3 Drawing Sheets

MARKER AND SIGNAL DEVICE FOR INDICATING THE PRESENCE OF A LASER

CROSS-REFERENCE TO RELATED APPLICATION

This application claims the benefit of priority of U.S. provisional application No. 63/200,586, filed Mar. 16, 2021, the contents of which are herein incorporated by reference.

BACKGROUND OF THE INVENTION

The present invention relates to medical markers and, more particularly, to a medical marker/signal device to assist in aiming a C-arm X-ray machine in a surgical operating room on a patient.

In an operating room, C-arm X-ray machine operators often do not have a line of sight to the exact point they are to align the C-arm to take an X-ray. Before the present invention, there were no markers to increase accuracy, decrease the number of shots and corrections, and reduce X-ray exposure.

Currently, the laser alone on the C-arm X-ray machine requires line of sight and without a line of sight requires timely adjustments that have greater error. Taking X-rays that are not correctly aligned with the target location can be necessary to find the correct alignment but expose the patient and medical practitioners to additional radiation.

Exposure to X-ray machines (technically called fluoroscopic equipment), especially in hospitals and surgery locations, is measured by "fluoroscopy time" or "fluoro time" for short. Fluoro time is an administrative record regulated by numerous government and non-government groups whose goal is to record and limit the dosage and timed exposure of employees, contractors, and patients to radiation from X-ray machines. If this allotted dosage is exceeded, it can be physically detrimental from radiation poisoning, damage to vital and reproductive organs, and cancer. As fluoroscopic equipment is necessary for many surgeries, reducing fluoroscopy time has taken on greater importance for the safety of those who use the equipment in their work and the patient.

As can be seen, there is a need for a medical marker/signal device to assist in aiming a C-arm X-ray machine in a surgical operating room on a patient.

SUMMARY OF THE INVENTION

In one aspect of the present invention, a marker and signal device for positioning a laser, the device comprising: a marker configured be positioned on a body of a patient, the marker comprising at least one sensor operable to selectively sense when the laser is pointed on the marker; and a signal emitter operably coupled with the marker and configured to emit an observable signal when the one or more sensors senses the laser on the marker.

In another aspect of the present invention, a system for positioning a laser, the system comprising: an C-arm X-ray machine configured to emit the laser; and a marker and signal device for positioning the laser, the device comprising: a marker configured be positioned on a body of a patient, the marker comprising at least one sensor operable to selectively sense when the laser is pointed on the marker; and a signal emitter operably coupled with the marker and configured to emit an observable signal when the one or more sensors senses the laser on the marker.

These and other features, aspects and advantages of the present invention will become better understood with reference to the following drawings, description, and claims.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, without departing from the scope of this disclosure.

DETAILED DESCRIPTION OF THE INVENTION

Figure 1:
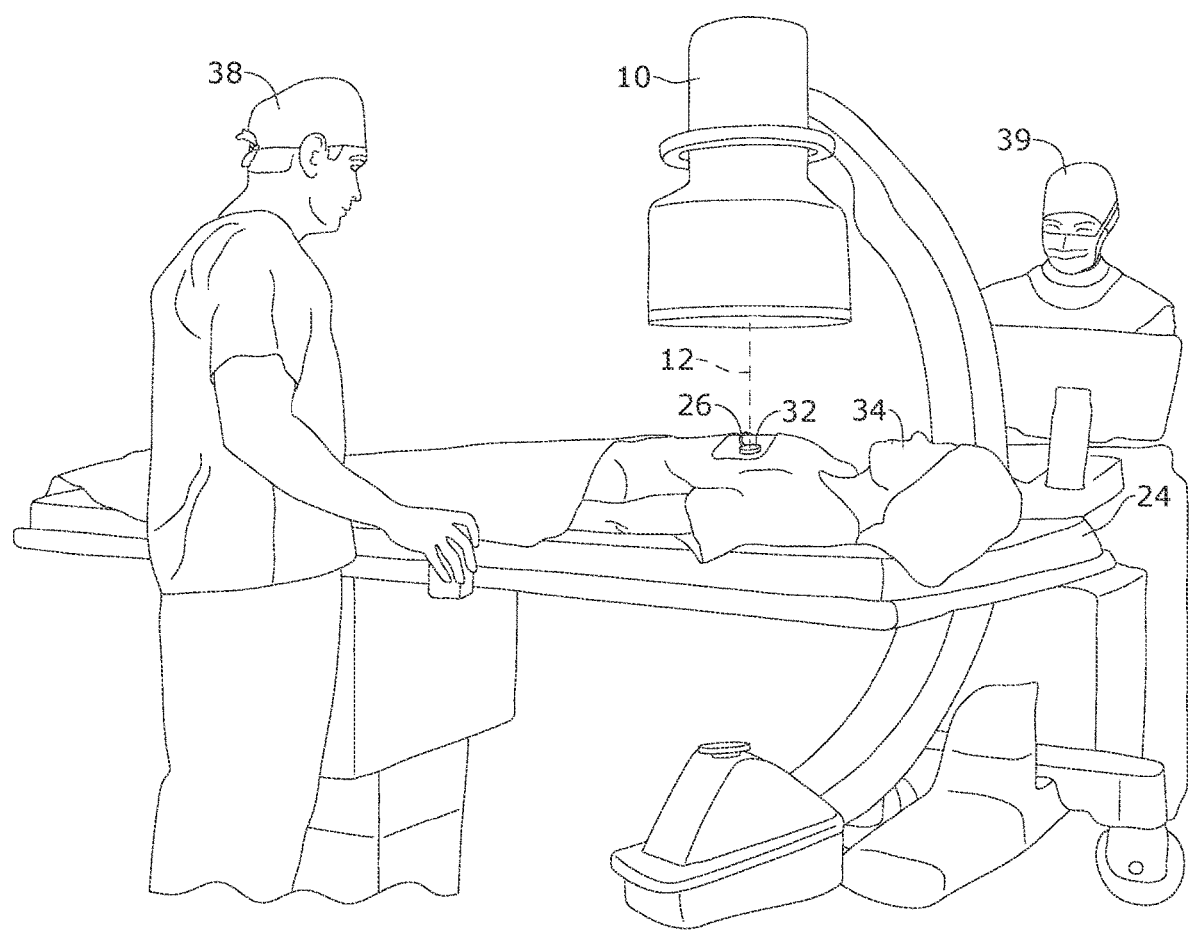
FIG. 1 is a perspective view of an embodiment of the present invention, shown in use.
Figure 2:
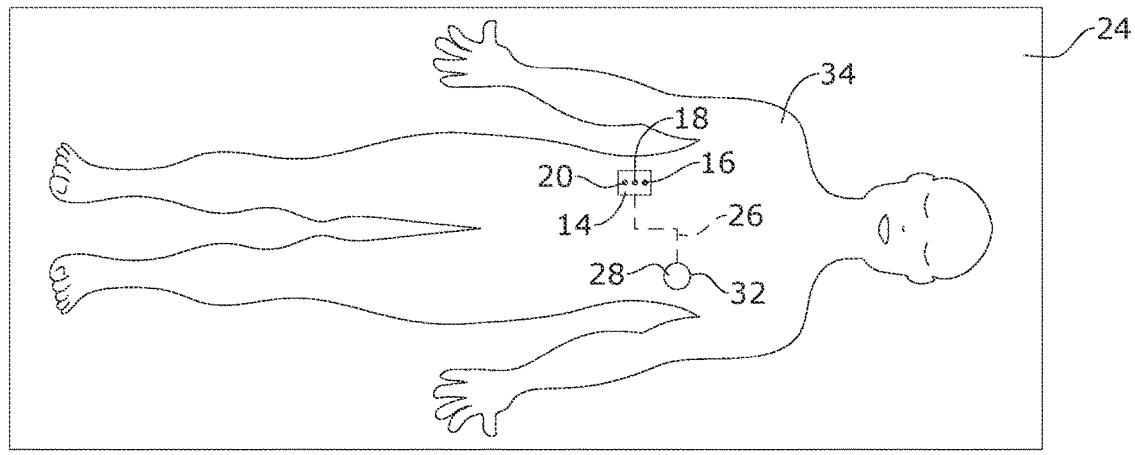
FIG. 2 is a top schematic view of the embodiment of the present invention.

The subject disclosure is described with reference to the drawings, wherein like reference numerals are used to refer to like elements throughout. In the following description, for purposes of explanation, numerous specific details are set forth in order to provide a thorough understanding of the present disclosure such that one skilled in the art will be enabled to make and use the present invention. It may be evident, however, that the present disclosure may be practiced without some of these specific details.

Broadly, an embodiment of the present invention provides an apparatus for signaling the placement of a laser, the apparatus including (1) a marker configured to selectively signal when the laser is pointed on the marker and (2) a signal in communication with the marker and configured to deliver an observable signal when the laser is pointed on the marker.

The marker of the present invention allows a C-arm X-ray machine operator to, with little or no communication with the surgeon, align the C-arm X-ray machine to near and then on target without a line of sight between the C-arm operator and the target location while operating and adjusting the C-arm X-ray machine.

Currently (before the present invention), the surgeon places a body-pen "dot" on the patient or an "X" where the C-arm X-ray machine operator is to line up the C-arm X-ray machine targeting laser. Still, no device assists in lining up the laser with the correct spot when there is no line of sight. The marker, as herein described, allows the C-arm X-ray machine operator to find the near location and on-target location without a direct line of sight.

In accordance with the present invention, the marker is to be placed on the patient. It would respond to being "hit" with the targeting laser of the C-arm, thereby letting the C-arm operator know when the C-arm's aim is closing and then on target to the proper X-ray position. Specifically, when the C-arm targeting laser is near the X-ray location, it will hit the edge of the marker. The marker will then signal that the laser is close to the intended X-ray location. The C-arm operator can adjust their aim, and when the targeting laser is directly on target with the marker, the marker will emit a different visible signal that the C-arm is precisely on target. Consequently, accuracy is increased, the number of shots, corrections needed is decreased, and overall X-ray exposure is minimized.

All components broadly listed are critical aspects of the present invention. Still, the diffuser material or the fiber optic could be used to solve the same material function of accomplishing funneling of the C-arm laser light into the marker's laser receiver sensors. As would be readily appreciated by those with skill in the art, other appropriate means of funneling the laser light into the laser receiver sensors may be employed, such as but not limited to a holographic card. A protruding wire with a light-emitting diode (LED) signal may be hardwired or plugged in to signal the C-arm operator who does not have a direct line of sight with the marker.

Figure 3:
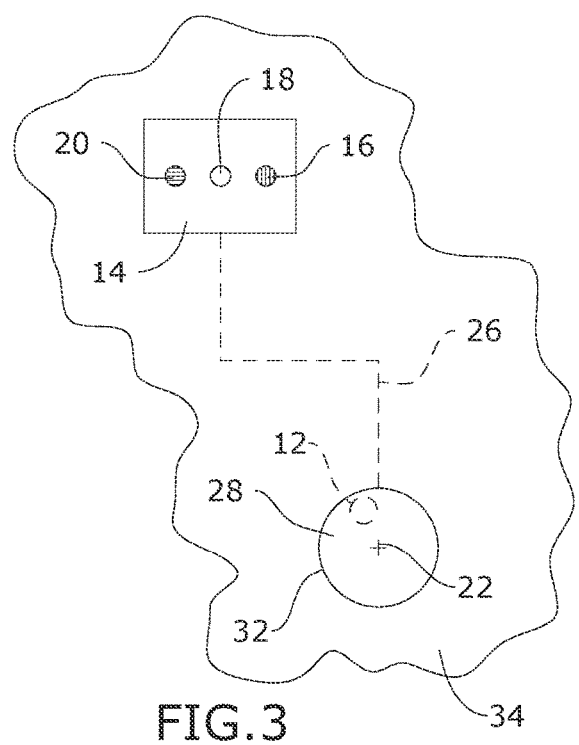
FIG. 3 is a detailed view of the top schematic view of the embodiment of the present invention, showing the on-target light.

Making reference now to FIG. 3, embodiments of the present invention generally include a marker 28 operably connected to a signal 14. In certain embodiments, the marker 28 and signal may be connected via a wire 26, while in other embodiments, the marker 28 and signal 14 (also referred to herein as a signal emitter) may be provided in wireless communication with one another.

Figure 7:
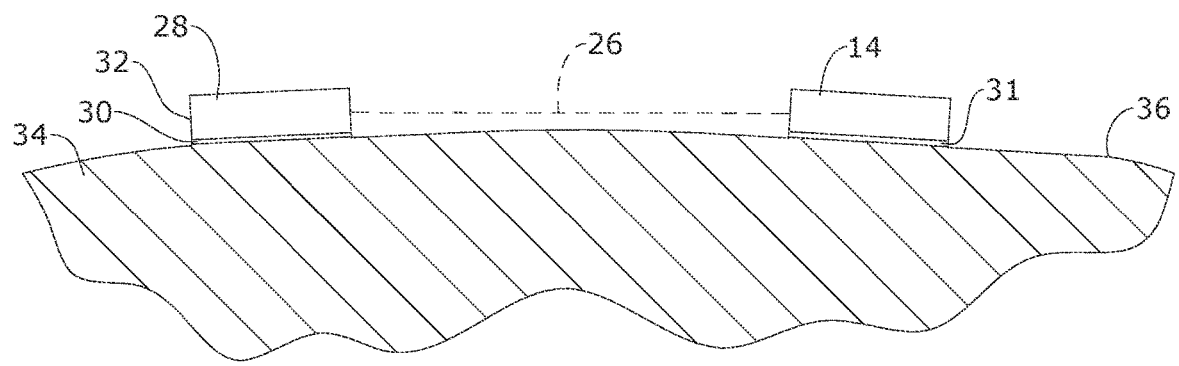
FIG. 7 is a detail view taken along line 7-7 in FIG. 5.

The marker 28 is equipped with a plurality of laser receiver sensors for detecting the presence of a laser 12 from a medical imaging device, embodied as a C-arm X-ray machine 10. As shown in FIG. 7, the marker 28 may be provided with an adhesive backing 30 to be secured in the proper location to the skin 36 of a patient 34. The marker 28 may be embodied as diffuser plastic 32 or another polymer medium. The marker 28 may alternatively be embodied as a fiber optic cable. The marker 28 may include a mark 22 that is indicative of a central location of the marker 28.

In certain embodiments, the signal 14 may include one or more LED lights 16, 18, 20, and may be battery-powered or powered by any other appropriate power source. Certain LED lights 18, 20 may be used to signal the marker's near position (e.g., near position light 18) and on-target position (e.g., on-target light 20). Another LED light 16 may be provided to indicate the signal 14 and marker 28 are on. The signal 14 is positioned such that it is easily visible to the C-arm operator 39, such as on a visible portion of the patent 34 and may be secured to the skin 36 patient 34 via an adhesive 31.

In use, as depicted in FIGS. 1-7, a patient 34 lies on a surface 24. The C-arm X-ray machine emits a targeting laser 12 onto the marker 28. This laser 12 is funneled to the laser receiver sensor(s), which in turn activates the signal 14 indicating that the laser 12 is hitting the marker 28. As mentioned above, the adhesive 30 retains the marker 28 on the medical patient's body 34 in the correct position, thereby marking the correct location of the body 34 at which the X-ray is to be taken.

In certain embodiments, the marker 28 may be a coin, cone, or cylinder shape that comprises the diffuser material 32 or fiber optic cable, which constitutes the exterior of the marker 28. The diffuser material 32 or fiber optic cable(s) directs the C-arm laser light 12 into a sensor wired to a battery, a signal 14, and a computer chip (not shown), functioning as a processor to govern the light or signal emissions of the signal 14 based on information received from the sensors on the marker 28.

Figure 4:
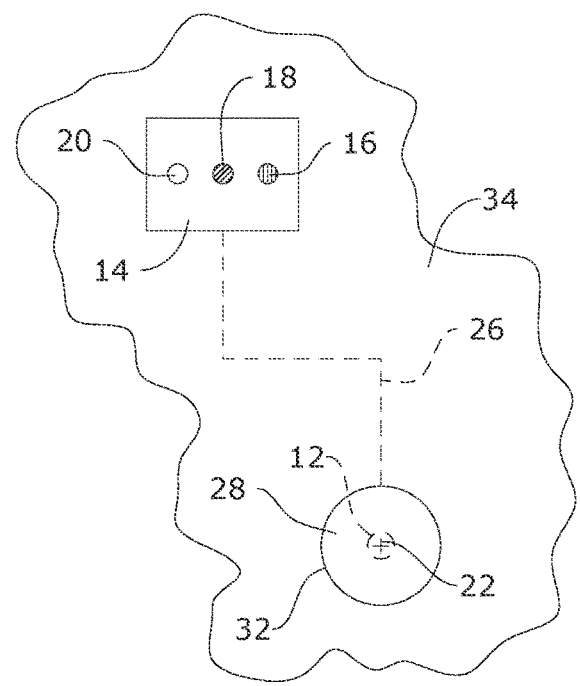
FIG. 4 is a detailed view of the top schematic view, showing the off-target light.
Figure 5:
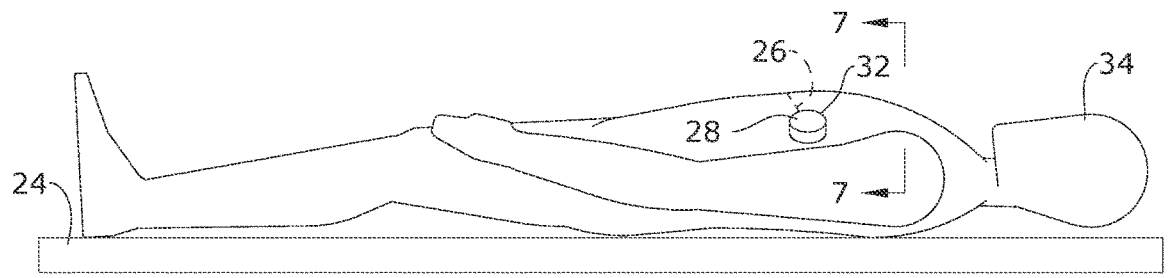
FIG. 5 is a side schematic view of the embodiment of the present invention, shown from a surgeon side.
Figure 6:
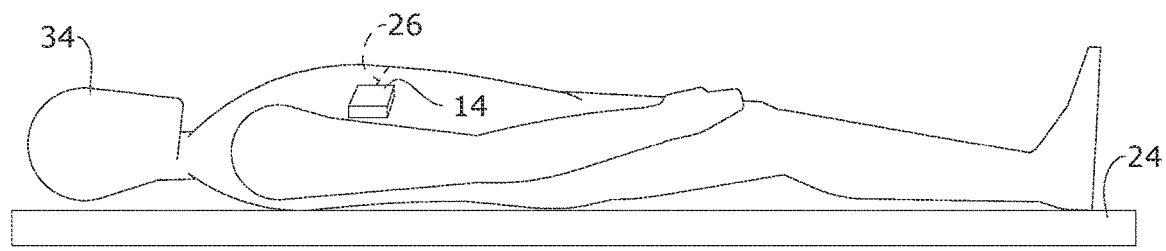
FIG. 6 is a side schematic view of the embodiment of the present invention, shown from a machine operator side.

By way of example, if the "near" sensor is struck (e.g., FIG. 3 is representative of this), then the "near" LED 18 is turned on. Alternatively, if the "on target" sensor is struck (e.g., FIG. 4 is representative of this), then the "on target" colored LED 20 is turned on, etc. As shown in FIG. 4, the laser 12 is properly positioned when it aligns with the mark 22. Since this mark 22 is not always visible to the C-arm operator 39, the signal 14 serves to provide an indication to the operator 39 that the laser 12 is or is not in the correct location. FIG. 6 is illustrative of this (the mark 22 not being readily visible, while the signal 14 is). It will be appreciated that while the drawings show distinct lights 18, 20, a single light may be provided that changes color, the color representing the proximity of the laser 12 to its intended mark 22.

The general logic of the system may include the following. If the marker 28 is turned on, it will signal "on" with an LED light 16. If the C-arm laser 41 is not hitting the marker 28 and the marker and signal device is on, it will simply give the "on" LED light signal 16 (such as a certain color LED). If the C-arm laser 12 hits the edge of the marker 28 but not at the on-target location (such as the blue/off-center laser lines seen in FIGS. 2 and 3), the marker 28 will signal a "near" visible signal emitted via the LED 18 (such as a second color LED). If the laser 41 is precisely on target (i.e., the laser 41 is directed towards a center portion or mark 22 of the marker 28), the marker 28 will emit an "on target" signal via the LED 20 that is different than the "near" signal 18 (such as a third color LED).

While a person of ordinary skill would understand how to make an embodiment of the present invention from the foregoing, a further method of making the present invention may include the following. The components described above may be soldered, plastic molded, printed, or fitted together. The diffuser may be 3D-printed or injection plastic molded and the fiber optic cable could be sourced from pre-manufactured sourced parts.

Besides the above, an exemplary method of using the present invention may include the following. First, find the spot where the C-arm X-ray machine 10 is to take its exact X-ray aim point(s). Second, remove the marker 28 from the packaging. Third, remove the adhesive backer to expose the adhesive 30. Fourth, apply the marker 28, with the adhesive side facing the patient 34, to the patient 34 directly over the aim point against the patient's skin 36. Fifth, apply any protruding LED/signal 14, which is operably connected to the marker 28, to the patient 34. This signal 14 will indicate to the C-arm operator 39 when they are near and on-target with the marker 28. Sixth, test the C-arm X-ray machine aiming laser 12 with the marker 28 to ensure that the off, near, and on-target signals are working. Seventh, proceed with the surgery, with the operator 39 utilizing the marker to aid in C-arm X-ray accuracy such that the surgeon 38 can concentrate on the surgery.

Besides the application just described, embodiments of the present invention could be used in any application in which a laser is used to guide a machine on-target when the machine operator does not have a direct line of sight with their target location of the machine's use.

While one or more preferred embodiments are disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

While apparatuses and methods are described in terms of "comprising," "containing," or "including" various components or steps, the apparatuses and methods can also "consist essentially of" or "consist of" the various components and steps. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

What is claimed is:

1. A marker and signal device for positioning a laser, the device comprising:

a marker configured be positioned on a body of a patient, the marker comprising at least one sensor operable to selectively sense when the laser is pointed on the marker; and a signal emitter operably coupled with the marker and configured to emit an observable signal when the one or more sensors senses the laser on the marker, wherein the signal emitter comprises one or more lights, and wherein the marker comprises a center point, and the signal emitter is configured to selectively emit, as the observable signal, a first color light when the laser is not pointed on the marker, a second color light when the laser is pointed on the marker away from the center point, and a third color light when the laser is pointed on the center point.

2. The marker and signal device of claim 1, wherein the at least one sensor is a plurality of sensors, and a position of the laser on the marker is at least partially determined by which sensor is struck.

3. The marker and signal device of claim 1, wherein the signal emitter is configured to be positioned on the body of the patient and spaced from the marker.

4. The marker and signal device of claim 1, wherein the marker comprises a diffuser material.

5. The marker and signal device of claim 1, wherein the marker comprises a fiber optic cable.

* * * * *